United States Patent [19]

Nakayama et al.

[11] Patent Number: 4,918,012
[45] Date of Patent: Apr. 17, 1990

[54] METHOD FOR PRODUCING CARNITINE, L-CARNITINAMIDE HYDROLASE AND METHOD FOR PRODUCING SAME

[75] Inventors: Kiyoshi Nakayama; Haruo Honda; Yukie Ogawa; Tatsuya Ozawa; Tetsuo Ohta, all of Kanagawa, Japan

[73] Assignee: Kyowa Hakko Kogyo Co., Ltd., Tokyo, Japan

[21] Appl. No.: 89,454

[22] Filed: Aug. 26, 1987

[30] Foreign Application Priority Data

Aug. 26, 1986 [JP] Japan ................................. 61-198173
Apr. 16, 1987 [JP] Japan ................................. 62-91938

[51] Int. Cl.$^4$ ...................... C12P 13/00; C12P 41/00; C12N 9/80
[52] U.S. Cl. .................................... 435/128; 435/228; 435/280; 435/874
[58] Field of Search ............... 435/228, 874, 128, 129, 435/280

[56] References Cited

U.S. PATENT DOCUMENTS

| 4,371,618 | 2/1983 | Cavazza | 435/128 |
| 4,636,471 | 1/1987 | Nakamura et al. | 435/280 |
| 4,642,290 | 2/1987 | Sih | 435/128 |
| 4,650,759 | 3/1987 | Yokozeki et al. | 435/128 |
| 4,751,182 | 6/1988 | Sih | 435/128 |

FOREIGN PATENT DOCUMENTS 2025412 1/1980 United Kingdom .

OTHER PUBLICATIONS

Nakayama, K. et al. (1988), Chem. Abst., 108:130065j.
Dunn, W. A. et al. (1981), J. Biol. Chem., 256(23), 12437–12444.

Primary Examiner—Thomas G. Wiseman
Assistant Examiner—Charles L. Patterson, Jr.
Attorney, Agent, or Firm—Sughrue, Mion, Zinn, Macpeak & Seas

[57] ABSTRACT

This invention relates to a method for producing carnitine comprising contacting, in a reaction medium, carnitinamide with (A) an amidase capable of hydrolyzing carnitinamide to form carnitine or (B) a microorganism containing said amidase, carnitinamide hydrolase and a method for producing same.

14 Claims, No Drawings

METHOD FOR PRODUCING CARNITINE, L-CARNITINAMIDE HYDROLASE AND METHOD FOR PRODUCING SAME

FIELD OF THE INVENTION

The present invention relates to a method for producing carnitine by hydrolyzing carnitinamide. The present invention also relates to an enzyme catalyzing a reaction in which L-carnitinamide is hydrolyzed into L-carnitine and a method for producing the enzyme.

BACKGROUND OF THE INVENTION

Carnitine, once referred to as vitamin $B_T$, is a substance participating in the metabolism of fatty acids and the DL-form thereof has heretofore been used as a stomachic. Recently, attention has been directed particularly to L-form thereof.

L-Carnitine is a substance indispensable for the transportation of fatty acids to mitochondria and is used as a transfusion component in the therapy of heart disorders, lipemia, etc. It is also useful as an intermediate for the production of other useful substances such as acetyl-L-carnitine.

For a long time, a chemical synthetic method has been known for the production of carnitine. However, this method is disadvantageous, from the viewpoints of energy consumption and environmental pollution, since it involves heating and use of mineral acids, alkalis or toxic substances and since the resulting carnitine is in the DL-form. Further, L-carnitine has heretofore been produced by optically separating DL-carnitine, obtained by the chemical synthetic method, using a diastereomer method.

Recently, various biochemical approaches have been developed for the production of L-carnitine, for example, hydroxylation of 4-N-trimethylaminobutyric acid (*J. Biol. Chem.*, 256, 1247 (1981)), reduction of 3-dehydrocarnitine (*Appl. Environm. Microbiol.*, 39, 329 (1980)), a method using 4-chloro-3-hydroxybutyric acid ester (Japanese patent application (OPI) No. 118093/84 (the term "OPI" as used herein refers to a "published unexamined Japanese patent application")), a method using crotonobetain as a substrate (Japanese patent application (OPI) Nos. 183694/84 and 118093/84), a method in which DL-O-acylcarnitine is hydrolyzed with an esterase (*Biotechnol. Bioeng.*, 26, 911 (1984)), etc.

These methods are disadvantageous from an industrial viewpoint since the starting materials used are expensive, the enzymes used are unstable and supply of expensive coenzymes is required. Although hydrolysis of carnitinamide with a mineral acid or the like has been known, biochemical hydrolysis of carnitinamide has not heretofore been known.

Further, to date, there have been no reports on a carnitinamide hydrolase which can be used in the production of intermediates for the synthesis of DL-carnitine.

SUMMARY OF THE INVENTION

An object of the present invention is to overcome the above-described disadvantages of the prior art and provide a method for producing L-carnitine biochemically.

Another object of the present invention is to provide a novel enzyme useful in the biochemical production of L-carnitine and a method for efficiently producing the enzyme.

Noticing the usefulness of carnitine, particularly its optically active isomer, L-carnitine, intensive investigation has been made on a biochemical method for producing carnitine directly from carnitinamide, the most efficient intermediate for the chemical synthesis of carnitine starting from epichlorohydrin. Not only have microorganisms from culture collections been investigated but also newly isolated microorganisms have been investigated for an appropriate enzyme. As a result, a novel enzyme, amidase, more specifically carnitinamide hydrolase, has been found in the present invention which is useful in the biochemical hydrolysis of carnitinamide to obtain carnitine, and a method for producing this enzyme efficiently has been also found in the present invention.

Therefore, in one embodiment, the present invention provides a method for producing carnitine comprising hydrolyzing carnitinamide by contacting, in a reaction medium, carnitinamide with (A) an amidase capable of hydrolyzing carnitinamide to form carnitine or (B) a microorganism containing said amidase.

In another embodiment, the present invention provides an amidase capable of hydrolyzing carnitinamide to produce carnitine.

In still another embodiment, the present invention provides a method for producing an amidase capable of hydrolyzing carnitinamide to produce carnitine by cultivating a microorganism capable of producing the amidase in the presence of a certain organic substance.

DETAILED DESCRIPTION OF THE INVENTION

There are two types of carnitinamide hydrolases. One is L-carnitinamide hydrolase capable of hydrolyzing L-carnitinamide to form L-carnitine and the other D-carnitinamide hydrolase capable of hydrolyzing D-carnitinamide to form D-carnitine.

The microorganisms which can be used in the present invention contain both types of carnitinamide hydrolases, the ratio of the activity of L-carnitinamide hydrolase to that of D-carnitinamide hydrolase varies widely (i.e., from 100% to 0%) depending on the strain and the growth conditions.

The enzyme used in the method of the present invention is an enzyme capable of hydrolyzing carnitinamide to produce carnitine and is generally called amidase. The amidase is classified in the group of hydrolases which act on linear amide bonds (Class 3.5.1) according to the nomenclature of the international enzyme classification, and more specifically named as carnitinamide hydrolase. Heretofore, there has been no reports on amidases acting on those compounds having a trimethylamino group in the molecule, such as carnitinamide. Such enzymes have been found for the first time in the present invention.

Microorganisms which produce an enzyme capable of converting carnitinamide into carnitine can be selectively isolated based on the capability of producing carnitine from carnitinamide.

Examples of such microorganisms include bacteria belonging to the genus Pseudomonas, e.g., Pseudomonas sp. CA27B1 (FERM BP-1380), Pseudomonas sp. CA30-11B (FERM BP-1378), Pseudomonas sp. CA28-50A (FERM BP-1377), Pseudomonas sp. CA10-1-5 (FERM BP-1376), Pseudomonas sp. CA32-C (FERM BP-1379) and Pseudomonas sp. CA30-35 (FERM BP-1375).

The taxonomic characteristics of these strains are as described hereinbelow.

The isolated strains are all Gram-negative aerobic bacilli. According to Bergey's Manual of Systematic Bacteriology, Vol. 1 (1984), they are considered to belong to the genus Pseudomonas in the family Pseudomonadaceae described in the section 4 of the Bergey's Manual.

Hereinafter, the taxonomic characteristics of the isolated strains will be explained by separating the strains into several groups based on some common characteristics.

First the characteristics which are common to all of the isolated strains are that they are Gram-negative aerobic rods and their cell size ranges from relatively small (0.5–0.8×0.7–3.0 μm) to relatively large (1.2–1.5×2.4–4.2 μm) as shown in Table 1 below. The strains show no polymorphism nor acid fastness under ordinary conditions. They do not form spores. They are motile by polar flagella. On a bouillon-agar medium they form small colonies which have entire edges with elevation of convex form. The surface thereof is smooth. The luster is translucent, milky white to grayish white (only CA30-35 has a yellow colony color). In a liquid bouillon medium, no surface growth is observed but the medium becomes moderately turbid after growth. Some strains (those belong to Group V of which CA32-C strain is typical) produce flaky precipitates but other strains produce no precipitate.

Gelatin liquefaction does not occur. The MR test, VP test, indole synthesis and starch hydrolysis are negative for all of the strains. Utilization of an inorganic nitrogen source (nitrates and ammonium salts) is positive for all of the strains on succinic acid medium. Oxidase and catalase are both positive. The O-F test is oxidative. Utilization of citric acid is positive for all of the strains on Simon medium. In litmus milk, the strains belonging to Group I, represented by CA27B1, render the milk alkaline and reduce litmus whereas other strains show no change (nor coagulation or liquefaction).

Acid formation from sugars is as shown in Table 1 below. In addition, acid formation by the strains other than CA30-35 is negative for L-arabinose, D-mannose, D-fructose, sucrose, maltose, p-trehalose, D-sorbitol, glycerol and starch.

Table 1 below shows the taxonomic characteristics of the above-described strains grouped into Groups I, II, III, IV, V and VI based on further common characteristics.

TABLE 1

| Characteristics | Group I | Group II | Group III | Group IV | Group V | Group VI |
|---|---|---|---|---|---|---|
| Formation of water-soluble pigment | + | − | + | − | − | −* |
| Formation of urease | − | − | − | − | + | − |
| Formation of hydrogen disulfide | − | + | − | − | + | + |
| Denitrification | − | − | − | − | + | − |
| Reduction of nitrate | + | + | + | + | − | − |
| Cell size | 1.2–1.5 × 2.4–4.2 | 1.2–1.5 × 2.1–3.6 | 1.2–1.4 × 2.1–2.8 | 0.7–1.1 × 2.0–4.0 | 0.5–0.8 × 0.7–3.0 | 0.6–0.8 × 1.1–1.3 |
| Growth pH | 6–9 | 5–9 | 6–9 | 6–9 | 6–9 | 6–9 |
| Optimum growth temperature (°C.) | 26–30 | 26–30 | 26–30 | 26–30 | 26–30 | 26–30 |
| Growth at 41° C. | − | − | − | − | ± | − |
| Growth at 4° C. | + | + | + | ++ | − | + |
| Growth at 37° C. | ± | ± | ± | ± | + | − |
| Accumulation of poly-β-hydroxybutyric acid | + | + | + | + | − | − |
| Acid formation from sugar | | | | | | |
| D-Glucose | + | + | + | − | − | + |
| D-Xylase | + | + | − | − | − | + |
| D-Galactose | − | − | − | − | − | + |
| Lactose | − | − | − | − | − | − |
| Assimilation of carbon source (Iizuka & Komagata method)*** | | | | | | |
| Mesoinositol | ± | − | + | + | + | − |
| Glucose | + | + | + | + | + | + |
| Trehalose | ± | + | + | + | + | + |
| Arginine | + | + | − | + | + | − |
| 2-Ketogluconic acid | + | + | + | + | + | − |
| L-Valine | + | + | + | + | + | − |
| β-Alanine | + | + | + | + | + | − |
| Catechol | − | − | + | − | − | − |
| Protocatechuic acid | + | + | + | + | + | + |
| p-Hydroxybenzoic acid | − | − | −** | − | − | − |

Notes:
*Color of cells is yellow.
**"+" by Stainer method (Stainer, R. Y. et al., J. Gen. Microbiol, 4, 159 (1966))
***Iizuka, H. and Komagata, K., Nippon Noeikagaku Kaishi, 36, 663 (1962)

Several strains of the microorganisms having the above-described characteristics have been isolated for each of Groups I to VI.

Although the strains belonging to Group I have many characteristics common to *Pseudomonas putida* and *Pseudomonas delafieldii* they are different from *P. putida* in the accumulation of poly-β-hydroxybutyric acid and different from *P. delafieldii* in the formation of a water-soluble pigment and growth at 4° C. Since there was found no type strain to which the strains could correspond they were identified as Pseudomonas sp. and a typical strain CA27B1 was deposited at the Fermentation Research Institute, Agency of Industrial Science and Technology, Ministry of International Trade and Industry, Japan of 1-3, Higashi 1-chome, Yatabemachi, Tsukuba-gun, Ibaraki-ken, 305 Japan (hereinafter referred to as "Bikoken").

The strains belonging to Group II have many characteristics common to *P. delafieldii* but they are different from it in the assimilation of arginine and growth at 4° C. Formation of hydrogen disulfide is positive and growth at pH 5 is good. Since no type strain was found to which the above strains could correspond the strains were identified as Pseudomonas sp. and a typical strain CA30-11B was deposited at Bikoken.

Also, the strains belonging to Group III have many characteristics common to *P. delafieldii*. However, they are different from it in the formation of a watersoluble pigment and growth at 4° C. They were identified as Pseudomonas sp. since no type strain was found to which they could correspond. A typical strain CA28-50A was deposited at Bikoken.

The strains belonging to Group IV also have many characteristics common to *P. delafieldii* but are different from it in the assimilation of arginine and inositol and growth at 4° C. Since there was found no type strain to which they could correspond they were identified as Pseudomonas sp., and a typical strain CA10-1-5 was deposited at Bikoken.

Although the strains belonging to Group V resemble *Pseudomonas alcaligenes*, they differ from it in the assimilation of glucose and arginine. Since no other type strain was found to which they could correspond, they were identified as Pseudomonas sp. and a typical strain CA32-C was deposited at Bikoken.

The strains belong to Group VI could be identified as belonging to the genus Xanthomonas since they require a growth factor for their growth and the color of the cells is yellow. However, the absorption spectrum of the pigment does not coincide with that of xanthomonadin. Therefore, they were for the present considered to belong to the genus Pseudomonas. The strain of this group form acid from a variety of sugars such as L-arabinose, D-mannose, D-fructose, D-galactose, maltose, sucrose, trehalose, D-mannitol and inositol in addition to those described in Table 1 above. Since there was found no proper species in the genus Pseudomonas to which they could correspond they were identified as Pseudomonas sp. and a typical strain CA30-35 was deposited at Bikoken.

The correspondence between the names of the strains deposited at Bikoken and their accession numbers are as listed below.

| Name of Strain | Accession Number |
| --- | --- |
| CA27B1 | FERM BP-1380 |
| CA30-11B | FERM BP-1378 |
| CA28-50A | FERM BP-1377 |
| CA10-1-5 | FERM BP-1376 |
| CA32-C | FERM BP-1379 |
| CA30-35 | FERM BP-1375 |

These microorganisms can be wild strains or mutants. Strains containing genes coding for the amidase can also be used in the present invention.

The enzymes can be those extracted from the above-described microorganism cells or the culture broth. Immobilized enzymes and immobilized microorganisms containing the enzyme can also be employed as long as they exhibit amidase activity, more specifically carnitinamide hydrolase activity.

In order to obtain a culture containing a carnitinamide hydrolase activity by cultivating a microorganism capable of producing this enzyme, usual cultivation methods, can be used; namely, cultivating in a nutrient medium containing organic compound as a carbon source, organic or inorganic compounds as a nitrogen source, and mineral salts, at pH 4 to 9, at 10° to 40° C. It is preferred to add at least one compound selected from the group consisting of carnitinamide, carnitine and γ-butyrobetain since a culture having a high carnitinamide hydrolase activity can be obtained by the addition of such compound. The concentration of these compounds to be added in a medium is generally from about 0.1 to 3% by weight, preferably from about 0.5 to 2.0% by weight, based on the weight of the culture medium. The effect of these compounds is as shown in Example 9 hereinbelow from which it can be seen that the medium containing at least one such compound increases the yield of the enzyme remarkably.

Further, both solid medium and liquid medium can be used in the present invention.

Other conditions of cultivation of the enzymeproducing strains can be selected appropriately such that the strains used can grow well according to the knowledge of those skilled in the art.

Although upon prolonged cultivation or addition of a releasing agent the enzyme is usually released from the cells, the enzyme activity is present mainly inside the cells. After completion of the cultivation, the cells and insoluble matter were removed from the culture broth by centrifugation or filtration to obtain a crude enzyme solution. The carnitinamide hydrolase contained in the cells can be removed as a crude enzyme solution by destructing the cells by grinding or ultrasonication and extracting the enzyme therefrom. Of course, the cells as they are can be used as an enzyme preparation.

Purified carnitinamide hydrolase can be obtained from the crude enzyme solution by conventional enzyme purification methods such as an organic solvent fractionation method, an ammonium sulfate differential precipitation method, dialysis, isoelectric point precipitation method, and column chromatography alone or in combination. When a solid medium is used, water is added to the solid medium containing microbial cells, and the mixture as it is or after collecting the cells is subjected to the above-described ultrasonication or the like treatment to obtain a crude enzyme solution.

The substrate of L-carnitinamide hydrolase is L-carnitinamide and the enzyme does not act on D-carnitinamide, and thus when the enzyme is used on DL-carnitinamide, for example, L-carnitinamide is converted to L-carnitine and D-carnitinamide which is not susceptible to the action of the enzyme remains unchanged. By appropriate means the two compounds can be separated from each other to obtain L-carnitine and D-carnitinamide (which can be further converted to D-carnitine by a conventional method, if desired).

Of course, carnitinamide can be used in the form of a physiologically acceptable salt thereof, e.g., chloride and carnitine can be obtained in the form of a physiologically acceptable salt thereof, e.g., chloride or sulfate.

The microorganism cells having an amidase activity or enzyme preparation derived therefrom thus obtained can be contacted with the substrate by adding the enzyme preparation in a solution containing the substrate and incubating the reaction mixture until the reaction proceeds or by adding the substrate in a culture broth of the microorganism followed by incubation for reaction. Alternatively, the enzyme can be contacted with the substrate in the form of enzyme preparations or cells separated from a culture broth of the microorganism of the present invention, physicochemically or biochemically treated cells such as washed cells, lyophilized cells and acetone-dried cells, extract solutions, purified preparations, immobilized preparations, etc.

The concentration of the substrate varies depending on whether a batch system or a continuous system is used. In the batch system, it ranges generally from about 0.1 to 30%, preferably from about 0.5 to 10%, by weight based on the weight of the reaction medium. In the continuous system, slightly lower ranges of the concentration, namely 0.05 to 20% by weight, are preferred.

The reaction can be carried out usually at about 5° to 60° C., preferably about 25° to 40° C., at a pH about 4 to 10, preferably at a pH of about 6 to 8. The reaction time varies depending on the means of standing, stirring, flowing down through the column containing the immobilized enzyme, etc., or the form or activity of the enzyme but usually it ranges from about 1 to 100 hours.

The process of the reaction can be monitored by monitoring the generation of carnitine using thin layer chromatography or by analysis of the generation of L-carnitine according to Pearson's enzyme method (D. J. Pearson et al., Method in Enzymology, Vol. 14, 612 (1969)). The proportion of L-form/D-form in the total carnitine (L-form+D-form) or the optical purity can be determined by separating carnitine from the reaction mixture using silica gel chromatography, converting carnitine into carnitineamide of L-phenylalanine, carrying out high performance liquid chromatography, measuring the areas of the resulting chromatographs of L-carnitinamide of L-phenylalanine and of D-carnitinamide of L-phenylalanine and calculating the ratio of the areas. After completion of the reaction, the reaction mixture is passed through a column charged with an ion exchange resin, followed by elution, for example, with dilute hydrochloric acid and concentrated to recover L-carnitine chloride.

The determination of the activity of carnitinamide hydrolase can be carried out by measuring the amount of carnitine generated by, for example, Pearson's method (D. J. Pearson et al., Method in Enzymology, Vol. 14, 612 (1969)). When there is no inhibitory substances present, the determination of the activity of the enzyme can also be carried out by measuring the amount of ammonia generated by the reaction.

Hereinafter, the enzymological characteristics of L-carnitinamide hydrolase of the present invention will be explained.

(1) Action and Specificity:

The enzyme catalyzes a reaction in which L-carnitinamide is hydrolyzed to form L-carnitine and ammonia. It does not act on D-carnitinamide. It does not act on acetamide, butyramide, acrylamide, nicotinamide, benzamide, etc., and in this regard it is quite different from generally known amidases.

(2) Optimum pH:

The amounts of L-carnitine generated from 2% DL-carnitinamide after 1 hour's reaction at various pH values were measured and the results obtained are shown in Table 2 below. From the results in Table 2, the optimum pH is judged to be in the range of 6 to 7.

TABLE 2

| Reaction pH | Buffer Solution* | Amount of L-Carnitine Formed (mg/ml) |
|---|---|---|
| 3.0 | I | 0.007 |
| 4.0 | I | 0.011 |
| 5.0 | I | 0.270 |
| 6.0 | I | 0.677 |
| 7.0 | I | 0.706 |
| 7.0 | II | 0.712 |
| 8.0 | II | 0.519 |
| 8.0 | III | 0.274 |
| 9.0 | III | 0.083 |
| 10.0 | III | 0.053 |

*I: Citric acid-sodium phosphate buffer solution (100 mM)
II: Sodium phosphate-sodium hydroxide buffer solution (100 mM)
III: Boric acid-sodium chloride-sodium carbonate buffer solution (100 mM)

(3) pH Stability:

the enzyme is highly stable generally at pH 5 to 8 and particularly at pH 7 to 8.

(4) Optimum Temperature:

The enzyme acts well at 26° to 40° C. and its optimum temperature is about 40° C. At temperatures higher than 45° C. or at lower than 20° C. the activity decreases.

(5) Temperature Stability:

The enzyme is considerably stable at 26° C. or at 4° C. for 7 days and retains 62% and 92% activity, respectively, compared with the activity when stored at −70° C. At 45° C. or more the activity decreases rapidly.

(6) Molecular Weight:

The molecular weight of the enzyme obtained by the gel filtration method (using Cellulofine GC-700m) is about 36,000.

(7) Inhibitors:

In a concentration of 1 mM, Ag ion shows a slight inhibition but other metal ions (Cu, Fe, Mn, Mg, Zn, Co, Ni) show no inhibition. At 10 mM, Ag ion shows remarkable inhibition and Fe and Ni show slight inhibition. EDTA and 2-mercaptoethanol do not show inhibition at 1 mM and 10 mM.

According to the method of the present invention, the reaction can proceed under mild conditions, i.e., at room temperature and in the vicinity of neutral pH range, which is advantageous as compared with the conventional methods from the viewpoints of reduced energy consumption and prevention of environmental pollution. In contrast to the conventional biochemical methods using a compound derived from carnitine as a starting compound, the present invention enables one to produce optically active carnitine from optically inactive DL-carnitinamide which is an intermediate for the chemical synthesis of carnitine.

Hereinafter, the present invention will be described in greater detail with reference to examples which should by no means be construed as limiting the present invention thereto.

In the following examples all percentages are by weight unless otherwise indicated.

EXAMPLE 1

Big test tubes (2.4 cm × 19.5 cm) containing 5 ml of a medium consisting of 1% glucose, 0.1% ammonium chloride, 0.5% meat extract, 0.5% polypeptone, 0.75% dipotassium phosphate, 0.25% monopotassium phosphate, 0.01% magnesium sulfate heptahydrate, 0.01% ferrous sulfate heptahydrate, 0.5% sodium chloride, 1% DL-carnitinamide chloride and the balance water (pH 7.2) were sterilized. Then, the microorganisms shown in Table 3 below were inoculated and shake cultured at 26° C. for 72 hours. To the culture was added 0.5 ml of a phosphate buffer solution (pH 7.0) containing 100 mg/ml DL-carnitinamide chloride and the mixture was further incubated with shaking at 26° C. for 24 hours. As the result, L-carnitine (as the hydrochloride) was formed in the concentrations shown in Table 3 below.

TABLE 3

| Strain | L-Carnitine Hydrochloride (mg/ml) |
| --- | --- |
| CA27B1 | 3.1 |
| CA28-50A | 3.6 |

EXAMPLE 2

The same procedures as in Example 1 were repeated except that the strain CA30-35 was used as the microorganism and a medium consisting of 1% glucose, 0.5% polypeptone, 0.3% meat extract, 0.3% yeast extract, 0.25% sodium chloride and the balance water (pH 7.2) was used. In this case, the amount of L-carnitine formed in the medium was 5.8 mg/ml (as the hydrochloride). When the cultivation was continued for an additional 48 hours, the amount of L-carnitine formed was 8.9 mg/ml (as the hydrochloride). The proportion of L-form:D-form in the total carnitine in the culture medium was analyzed to be 91.5%:8.5%.

EXAMPLE 3

Cells were separated by centrifugation from the culture broth obtained after the cultivation of the microorganisms shown in Table 4 below for 72 hours in the same medium as used in Example 1 and washed twice. The cells were added to a phosphate buffer solution (pH 7.0) so that the cell density could be the same as that of the original culture medium, while DL-carnitinamide chloride was added in a concentration of 10 mg/ml. The resulting mixture was incubated with shaking at 26° C. for 24 hours. The amount of L-carnitine (as the hydrochloride) formed in the culture medium and the proportion of L-form in the carnitine in the culture medium are shown in Table 4 below.

TABLE 4

| Strain | Concentration of L-Carnitine (mg/ml) | Proportion of L-Form (%) |
| --- | --- | --- |
| CA27B1 | 4.6 | 98 |
| CA28-50A | 5.4 | 94 |

EXAMPLE 4

After cultivating the strains shown in Table 5 below for 72 hours in the same medium as used in Example 1, cells were collected by centrifugation from the culture broth and washed twice. Then, a phosphate buffer solution (pH 7.0) and also DL-carnitinamide chloride were added to the cells so that the cell density in the resulting mixture could be 10 times that of the original culture medium and the concentration of DL-carnitinamide was 10 mg/ml. The mixture was incubated with shaking at 26° C. for 18 hours for the reaction. The amount of L-carnitine (as the free compound) formed in the culture medium and the proportion of L-form in the total carnitine in the culture medium are shown in Table 5 below.

TABLE 5

| Strain | Concentration of L-Carnitine* (mg/ml) | Proportion of L-Form (%) |
| --- | --- | --- |
| CA30-35 | 0.26 | 89.5 |
| CA28-50A | 0.97 | 92.8 |
| CA30-11B | 0.32 | 47.0 |
| CA30-32B | 0.44 | 26.8 |
| CA32-C | 1.82 | 59.5 |
| CA10-1-5 | 1.13 | 41.8 |

EXAMPLE 5

The same procedures as in Example 3 were repeated except that the concentration of carnitinamide hydrochloride in the case of using the microbial cells per se was changed to 5%. The amount of L-carnitine (as the hydrochloride) after 72 hours of reaction was 1.20 mg/ml for the strain CA27B1 and 24.9 mg/ml for the strain CA28-50A.

EXAMPLE 6

Cells of the strain CA28-50A obtained by cultivating the microorganism in the same manner as in Example 1 were suspended in physiological saline in a density of 200 mg/ml and 10 ml of the suspension was mixed with 10 ml of a 4% sodium alginate solution. The resulting mixture was portionwise added to a 15% calcium chloride solution to obtain particulate immobilized cells. The total amount of the immobilized cells were added to 20 ml of a phosphate buffer solution (pH 7.0) containing 1% DL-carnitinamide chloride and allowed to stand at 30° C. for 16 hours for the reaction. As the result, 1.6 mg/ml of L-carnitine hydrochloride was formed.

EXAMPLE 7

In a 300 ml Erlenmeyer flask containing 30 ml of a medium consisting of 1% citric acid, 1% peptone, 0.5% meat extract, 0.5% sodium chloride, 0.75% dipotassium phosphate, 0.25% monopotassium phosphate, 0.01% magnesium sulfate heptahydrate, 0.001% ferrous sulfate heptahydrate, 0.5% carnitinamide chloride and the balance water (pH 7.2) was inoculated the strain CA28-50A and shake cultured at 26° C. for 3 days. Cells were collected from the culture broth by centrifugation and suspended in a phosphate buffer solution (pH 7.0) containing 10% DL-carnitinamide chloride (the same amount of the medium as the medium for growth culture), and the resulting suspension was allowed to stand at 26° C. for 96 hours for the reaction. As the result, 48.9 g/l of L-carnitine (as the hydrochloride) was formed.

EXAMPLE 8

In a medium consisting of 2% glucose, 2% corn steep liquor, 0.5% sodium chloride, 0.75% dipotassium phosphate, 0.25% monopotassium phosphate, 0.01% magnesium sulfate heptahydrate, 0.001% ferrous sulfate heptahydrate, 1% carnitinamide chloride and the balance water (pH 7.2) was inoculated the strain CA28-50A and shake cultured at 20° C. for 3 days. Cells were collected from the culture broth by centrifugation and suspended in a phosphate buffer solution (pH 7.0) containing 20% DL-carnitinamide chloride (the same amount of the medium as the medium for growth culture), and the resulting suspension was allowed to stand at 26° C. for 144 hours for the reaction. As the result, 97.6 g/l of L-carnitine (as the hydrochloride) was formed. The reaction mixture was passed through a strongly acidic ion exchange resin (sodium type) column to adsorb L-carnitine and carnitinamide, and then a 2% solution of ammonium acetate was passed through the column to separate L-carnitine from carnitinamide followed by concentrating the L-carnitine fraction and cooling it after adding alcohol, thus recovering L-carnitine.

EXAMPLE 9

In a medium consisting of 1% glucose, 0.5% peptone, 0.75% $K_2HPO_4$, 0.25% $KH_2PO_4$, 0.01% $MgSO_4.7H_2O$, 0.001% $FeSO_4.7H_2O$ and one of the compounds shown in Table 6 below and the balance water (pH 7.2) was inoculated the strain CA28-50A and shake cultured at 26° C. for 3 days. Cells collected from the culture broth by centrifugation were suspended in a reaction solution containing 10% DL-carnitinamide in the same density as that in the medium for growth culture, and the resulting suspension was allowed to stand at 26° C. for 96 hours for the reaction. The conversion rate of L-carnitinamide into L-carnitine is shown in Table 6 below.

TABLE 6

| Compound (concentration) | Growth* | Conversion Rate (%) |
|---|---|---|
| DL-Carnitinamide (0.5%) | 0.27 | 88.7 |
| DL-Carnitine (0.5%) | 0.27 | 90.0 |
| γ-Butyrobetaine (0.5%) | 0.26 | 12.3 |
| $NH_4Cl$ (0.1%) | 0.23 | 2.9 |

*20 times dilution, optical density transmitted through 1.00 cm at 660 mμ

EXAMPLE 10

Cells were collected from 800 ml of the culture broth obtained by cultivating the strain CA28-50A in the same medium as used in Example 9 containing 0.5% DL-carnitineamide and ground in a 10 mM phosphate buffer solution (pH 7.0) together with quartz sand followed by centrifugation to obtain 20 ml of a cell-free extract. To this was added 300 ml of a 50 mM phosphate buffer solution (pH 7.0), and ammonium sulfate was added thereto to 90% saturation to form a precipitate, which was then dissolved in 20 ml of a 50 mM phosphate buffer solution (pH 7.0). The solution obtained was dialyzed against the 50 mM phosphate buffer solution, and 40 ml of the resulting enzyme solution was passed through a Millipore membrane filter (Immersible C×10) at 4° C. for 24 hours to give 4 ml of a concentrated enzyme solution. This was subjected to gel chromatography using Cellulofine GC-700m (Chisso Co.) having a particle size of 45 to 105 μm (column: 10×520 mm; gel volume 70 ml), and then eluted with 0.05M Tris-HCl (pH 7.5)+0.1M KCl solution and 0.5 ml fractions were collected.

As the result, it was found that Fraction No. 51 showed the highest activity. This fraction had an O.D. at 280 ml of 0.039 and formed 0.593 mg/ml of L-carnitine by the reaction at 26° C. for 60 minutes. The specific activity (activity per unit O.D.) was 13.8, which was 4181 times the specific activity of cell extract.

EXAMPLE 11

Cells were collected by centrifugation from 300 ml of the culture broth obtained by cultivating the strain CA28-50A in the same medium as used in Example 9 containing 0.5% DL-carnitinamide and ground in a 50 mM phosphate buffer solution (pH 7.0) together with quartz sand followed by centrifugation to obtain 30 ml of a cell-free extract. Living cells and a cell-free extract were each added to a reaction solution containing 0.2% DL-carnitinamide in the same concentration as that in the growth culture medium in terms of the original cell amount and the resulting mixtures were allowed to stand for the reaction at 26° C. Analytical data on the reaction time and the amount of L-carnitine formed are shown in Table 7 below.

TABLE 7

| Sample | 0.5 Hr | 1.0 Hr | 1.5 Hrs | 2.0 Hrs | 3.0 Hrs | 19 Hrs |
|---|---|---|---|---|---|---|
| Cell | 0.122 | 0.201 | 0.233 | 0.323 | 0.378 | 0.866 |
| Extract | 0.145 | 0.298 | 0.273 | 0.340 | 0.427 | 0.852 |

From the data above, it was presumed that the reaction proceeds linearly until 0.5 hour and the titer of the enzyme in the cells per se and that in the extract were calculated from the reaction speed obtained from the above data. That is, the titer of the enzyme in the cells during growth culture per ml of the culture medium is 0.122 mg/ml÷161.2 μg (1 μmol of carnitine)÷60=0.125 μ/ml, and the titer of the enzyme in the extract is 0.145 mg/ml÷161 μg÷60=0.15 μ/ml.

EXAMPLE 12

The same procedures as in Example 9 were repeated except that the microorganisms as shown in Table 8 were used and DL-carnitinamide (0.5%) was the added compound to the basal growth medium. As the result, the formation of L-carnitine and D-carnitine is shown in Table 8. When DL-carnitinamide was not added and 0.1% $NH_4Cl$ was added to the growth medium, the formation of both L-carnitine and D-carnitine was less than 1.0 mg/ml.

TABLE 8

| | Formation of Carnitine (mg/ml) | | |
|---|---|---|---|
| Name of Strain | Total | L-Form | D-Form |
| CA27B1 | 43.4 | 41.3 | 2.1 |
| CA30-35 | 51.4 | 46.0 | 5.4 |
| CA30-11B | 35.7 | 16.8 | 18.9 |
| CA30-32B | 85.0 | 21.1 | 63.9 |
| CA32-C | 53.0 | 32.0 | 21.4 |
| CA10-1-5 | 51.0 | 19.5 | 31.5 |

From the above results, it can be seen that D-carnitine was formed from DL-carnitinamide, although the amount varied depending on the strain used. Consequently, together with L-carnitinamide hydrolase, the formation of D-carnitinamide hydrolase can be confirmed.

Furthermore, racemization of carnitine and carnitinamide by the microorganism did not occur.

Although the invention has been described with reference to preferred embodiments, it is to be understood that variations and modifications may be employed as will be apparent to those skilled in the art. Such variations and modifications are to be considered within the purview and scope of the claims appended hereto.

What is claimed is:

1. A method for producing carnitine comprising hydrolyzing carnitinamide by contacting, in a reaction medium, carnitinamide with (A) a carnitinamide hydrolase capable of hydrolyzing carnitinamide to form carnitine or (B) a microorganism containing said carnitinamide hydrolase.

2. The method as claimed in claim 1, wherein said carnitineamide is DL-carnitinamide and said carnitine is L-carnitine.

3. The method as claimed in claim 1, wherein said carnitinamide is L-carnitinamide and said carnitine is L-carnitine.

4. The method as claimed in claim 1, wherein said carnitinamide is D-carnitinamide and said carnitine is D-carnitine.

5. The method as claimed in claim 1, wherein said microorganism is a microorganism belonging to the genus Pseudomonas.

6. The method as claimed in claim 1, wherein said microorganism is a strain having the taxonomic characteristics of a strain selected from the group consisting of CA32-C (FERM BP-1379), CA10-1-5 (FERM BP-1376), CA27B1 (FERM BP-1380), CA30-11B (FERM BP-1378), CA28-50A (FERM BP-1377) and CA30-35 (FERM BP-1375).

7. The method as claimed in claim 1, wherein the hydrolyzing carnitinamide to form carnitine is performed at 5° to 60° C. and at a pH of 4 to 10 for 1 to 100 hours, with the concentration of said carnitinamide being 0.1 to 30% based on the weight of the reaction medium.

8. the method as claimed in claim 1, wherein said carnitinamide hydrolase has the following physiochemical characteristics:
(1) Action and Specificity:
hydrolyzes
L-carnitinamide to form L-carnitine and ammonia;
(2) Optimum pH and Stable pH Range:
Optimum pH: 6 to 7
Stable pH Range: 7 to 8;
(3) Optimum Temperature:
acts well at 26° to 40° C. and its optimum temperature is 40° C.;
(4) Conditions of Inactivation:
retains 90% or more of the activity at 4° C. for 7 days,
at 45° C. or more the activity decreases rapidly;
(5) Molecular Weight:
the molecular weight of the enzyme obtained by gel filtration (using Cellulofine GC-700m) is about 36,000; and
(6) Inhibitors:
inhibited with Ag ion at a high concentration (10 mM); and no inhibition with EDTA and 2-mercaptoethanol at 10 mM.

9. A carnitineamide hydrolase capable of catalyzing the hydrolysis reaction of L-carnitinamide to produce L-carnitine.

10. The carnitinamide hydrolase as claimed in claim 9, wherein said hydrolase has the following physiochemical characteristics:
(1) Action and Specificity:
hydrolyzes
L-carnitinamide to form L-carnitine and ammonia;
(2) Optimum pH and Stable pH Range:
Optimum pH: 6 to 7
Stable pH Range: 7 to 8;
(3) Optimum Temperature:
acts well at 26° to 40° C. and its optimum temperature is 40° C.;
(4) Conditions of Inactivation:
retains 90% or more of the activity at 4° C. for 7 days,
at 45° C. or more the activity decreases rapidly;
(5) Molecular Weight:
the molecular weight of the enzyme obtained by gel filtration (using Cellulofine GC-700m) is about 36,000; and
(6) Inhibitors:
inhibited with Ag ion at a high concentration (10 mM); and no inhibition with EDTA and 2-mercaptoethanol at 10 mM.

11. A method for producing an L-carnitinamide hydrolase comprising cultivating a microorganism which can produce an L-carnitinamide hydrolase capable of catalyzing the hydrolysis reaction of L-carnitinamide to produce L-carnitine in a medium containing at least one compound selected from the group consisting of carnitinamide, carnitine and γ-butyrobetaine.

12. The method as claimed in claim 11, wherein said microorganism is a microorganism belonging to the genus Pseudomonas.

13. The method as claimed in claim 12, wherein said microorganism is grown at 10° to 40° C. and at pH 4 to 9 in a nutrient medium containing carbon and nitrogen sources and mineral salts.

14. The method as claimed in claim 12, wherein said microorganism is a strain having the taxonomic characteristics of a strain selected from the group consisting of CA32-C (FERM BP-1379), CA10-1-5 (FERM BP-1376), CA27B1 (FERM BP-1380), CA30-11B (FERM BP-1378), CA28-50A (FERM BP-1377) and CA30-35 (FERM BP-1375).

* * * * *